(12) United States Patent
Beckers

(10) Patent No.: US 8,569,547 B2
(45) Date of Patent: Oct. 29, 2013

(54) PROCESS FOR RECOVERING MONOALKYLBENZENE

(75) Inventor: Johannes Gerhardus Joseph Beckers, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/517,251

(22) PCT Filed: Dec. 21, 2010

(86) PCT No.: PCT/EP2010/070330
§ 371 (c)(1),
(2), (4) Date: Jul. 24, 2012

(87) PCT Pub. No.: WO2011/076771
PCT Pub. Date: Jun. 30, 2011

(65) Prior Publication Data
US 2012/0283481 A1 Nov. 8, 2012

(30) Foreign Application Priority Data
Dec. 22, 2009 (EP) .................................. 09180283

(51) Int. Cl.
*C07C 7/10* (2006.01)
*C07C 409/02* (2006.01)

(52) U.S. Cl.
USPC .......................................... 568/569; 585/867

(58) Field of Classification Search
USPC .......................................... 568/569; 585/867
See application file for complete search history.

(56) References Cited

U.S. PATENT DOCUMENTS

| 3,592,857 A | 7/1971 | Shinohara ................. 260/610 B |
| 5,198,000 A | 3/1993 | Grasso et al. ..................... 55/20 |

FOREIGN PATENT DOCUMENTS

| WO | WO0005186 | 2/2000 | ............ C07C 15/146 |
| WO | WO02102496 | 12/2002 | ............ B01D 53/14 |
| WO | WO2006024655 | 3/2006 | ................ B01J 10/00 |
| WO | WO2008058925 | 5/2008 | ............ C07C 409/08 |

*Primary Examiner* — Sikarl Witherspoon

(57) ABSTRACT

The invention relates to a process for recovering monoalkylbenzene from a gas stream comprising oxygen and monoalkylbenzene, wherein the gas stream comprising oxygen and monoalkylbenzene is contacted with a liquid stream comprising a naphthalene compound. Further, the present invention relates to a process for preparing alkyl phenyl hydroperoxide incorporating said monoalkylbenzene recovery.

12 Claims, 1 Drawing Sheet

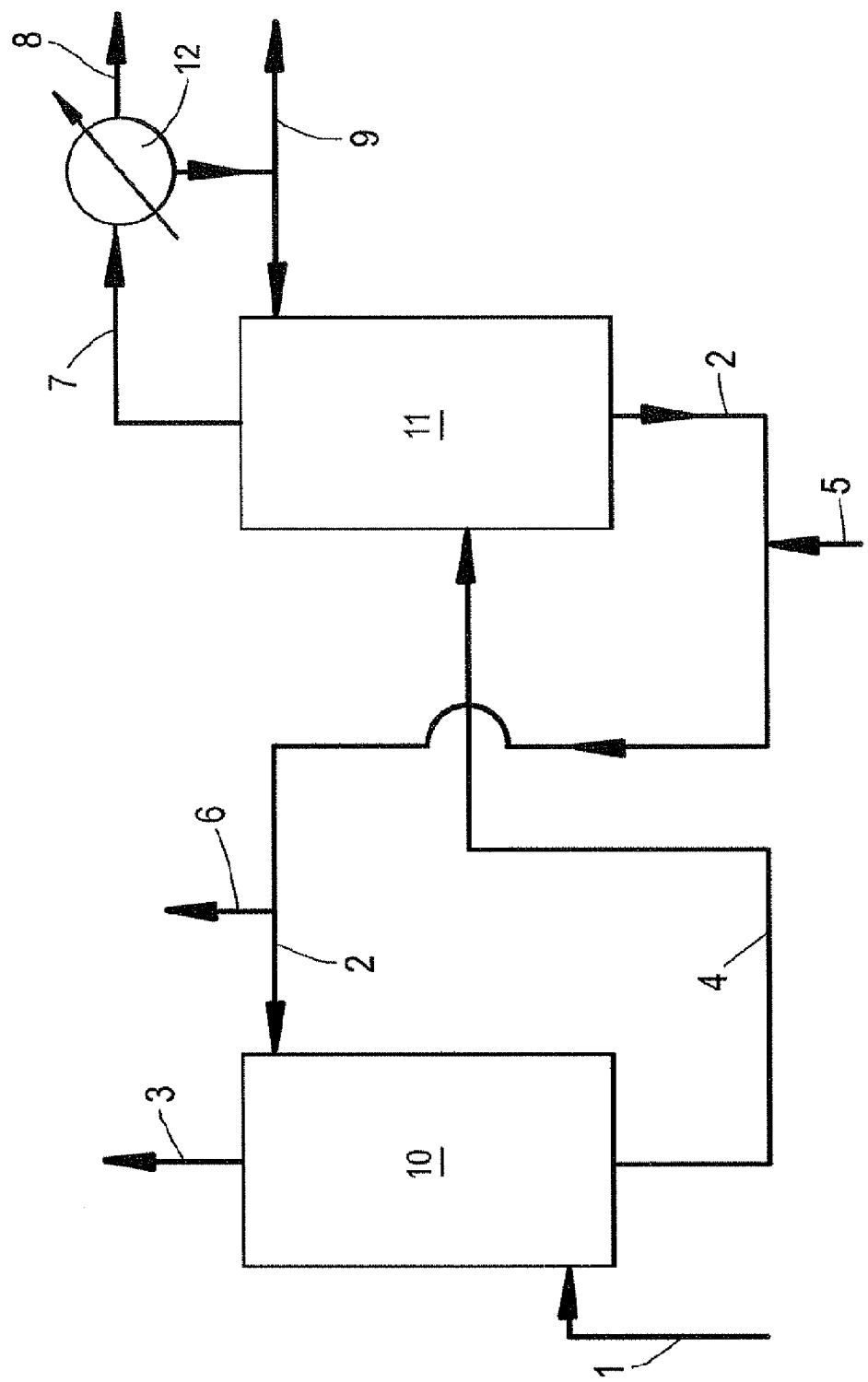

US 8,569,547 B2

PROCESS FOR RECOVERING MONOALKYLBENZENE

PRIORITY CLAIM

The present application claims priority from PCT/EP2010/070330, filed 21 Dec. 2010, which claims priority from 09180283.5, filed 22 Dec. 2009.

FIELD OF INVENTION

The present invention relates to a process for recovering monoalkylbenzene from a gas stream comprising oxygen and monoalkylbenzene. In addition, the present invention relates to a process for preparing alkyl phenyl hydroperoxide incorporating said monoalkylbenzene recovery.

BACKGROUND

Monoalkylbenzene can be used in the preparation of alkyl phenyl hydroperoxide. For example, ethylbenzene hydroperoxide can be prepared by the oxidation of ethylbenzene with oxygen containing gas, such as air. Such oxidation processes are well known in the art. An example thereof is described in U.S. Pat. No. 5,883,268. Other well-known processes wherein alkyl phenyl hydroperoxides are produced, are those wherein iso-propylbenzene (cumene) or sec-butylbenzene are oxidised, using oxygen containing gas, into the corresponding alkyl phenyl hydroperoxides.

Cumene hydroperoxide can subsequently be decomposed into phenol and acetone. Ethylbenzene hydroperoxide can subsequently be used in the oxidation of an alkene, such as propene, resulting in the production of alkene oxide (an oxirane or epoxide), such as propylene oxide, and methyl phenyl carbinol which is 1-phenylethanol. Methyl phenyl carbinol can then be dehydrated into styrene. Both the styrene and the propylene oxide are valuable market products.

Processes for the joint preparation of styrene monomer ("SM") and propylene oxide ("PO") are known in the art and are commonly referred to as "SM/PO" or "PO/SM" processes. An SM/PO process is for example described in WO200005186. In general, an SM/PO process comprises the steps of:
(a) reacting ethylene and benzene to form ethylbenzene;
(b) reacting ethylbenzene with oxygen containing gas to form ethylbenzene hydroperoxide;
(c) reacting ethylbenzene hydroperoxide with propene in the presence of an epoxidation catalyst to form propylene oxide and 1-phenylethanol; and
(d) dehydrating 1-phenylethanol into styrene in the presence of a suitable dehydration catalyst.

During said step (b) of oxidising ethylbenzene into ethylbenzene hydroperoxide, not all ethylbenzene reacts. Most of the ethylbenzene leaves the oxidation reactor as solvent for the ethylbenzene hydroperoxide. However, also a substantial portion of the ethylbenzene leaves the oxidation reactor as part of a gas stream comprising oxygen. Said gas stream comprising oxygen and ethylbenzene may be discarded. However, it would be advantageous to recover the valuable ethylbenzene from said gas stream comprising oxygen and ethylbenzene, and then re-use it for some purpose, for example by recycling the recovered ethylbenzene to the oxidation reactor.

However, in addition to oxygen and monoalkylbenzene (for example ethylbenzene) and an inert gas such as nitrogen, such gas stream comprising oxygen, nitrogen and monoalkylbenzene may comprise other contaminants, such as methane, water, acetaldehyde, propionaldehyde, methanol, benzene and toluene. These other contaminants should not be recovered from said gas stream together with the monoalkylbenzene. Therefore, the monoalkylbenzene should be recovered both efficiently and selectively from the gas stream comprising oxygen and monoalkylbenzene. Further, at the same time, in such recovery care should be taken of the presence of oxygen which is a reactive gas and not an inert gas such as nitrogen.

In general, it is known to absorb an organic contaminant from a gas stream comprising oxygen and organic contaminants, by contacting such gas stream with a liquid absorbent. For example, WO2002102496 discloses a process for the recovery of combustible components of a gas stream comprising the combustible components and oxygen by selective absorption of the combustible components in a solvent. The process of WO2002102496 is characterized in that during the absorption the gas phase is dispersed in a continuous liquid phase of the solvent. According to WO2002102496, said solvent (absorbent) may be selected from alcohols, aliphatic and aromatic hydrocarbons and ketones. Further, in Example 1 of WO2002102496, benzene is mentioned as a combustible component. Monoalkylbenzenes, such as ethylbenzene, are not disclosed in WO2002102496.

U.S. Pat. No. 5,198,000 on the other hand discloses a process wherein ethylbenzene is mentioned as one of the organic compounds that can be removed from a gas stream comprising oxygen and organic contaminants. The method of U.S. Pat. No. 5,198,000 is a method for removing volatile organic compounds from a contaminated air stream by contacting the latter with an absorbent to allow absorption of the volatile organic compound by the absorbent. Specific absorbents mentioned in U.S. Pat. No. 5,198,000 are motor oil, vegetable oil, corn oil, mineral oil, olive oil, castor oil, coconut oil, palm oil, peanut oil, safflower oil, soya bean oil, tucum oil, linseed oil and cotton seed oil. Corn oil is particularly preferred as the liquid absorbent of the invention of U.S. Pat. No. 5,198,000. According to U.S. Pat. No. 5,198,000, the source of the contaminated air stream may be off-gas produced by air stripping, flue gases, etc.

SUMMARY OF INVENTION

It is an object of the present invention to provide a process for recovering monoalkylbenzene from a gas stream comprising oxygen and monoalkylbenzene, wherein the monoalkylbenzene is recovered both efficiently and selectively from such gas stream, also taking into account the reactive nature of the oxygen in such gas stream, as discussed above. In addition, in a case where an absorbent comprising the absorbed monoalkylbenzene is not used as such in another process, such as for example the preparation of monoalkylbenzene by alkylation of benzene, the absorbent should be selected such that the monoalkylbenzene can be easily separated from the absorbent.

Surprisingly, it was found that monoalkylbenzene can be recovered in such way, both efficiently and selectively, from the gas stream comprising oxygen and monoalkylbenzene, by contacting said gas stream with a liquid stream comprising a naphthalene compound.

Accordingly, the present invention relates to a process for recovering monoalkylbenzene from a gas stream comprising oxygen and monoalkylbenzene, wherein the gas stream comprising oxygen and monoalkylbenzene is contacted with a liquid stream comprising a naphthalene compound.

DETAILED DESCRIPTION

In the process of the present invention, monoalkylbenzene is recovered from a gas stream comprising oxygen and monoalkylbenzene. Within this specification, "monoalkylbenzene" means benzene which is substituted with 1 alkyl substituent. Said alkyl substituent may be a linear or branched $C_1$-$C_6$ alkyl group, preferably a linear or branched $C_1$-$C_4$ alkyl group, such as ethyl, iso-propyl and sec-butyl. Where the alkyl substituent is iso-propyl, the monoalkylbenzene is also referred to as cumene rather than iso-propylbenzene. Preferably, the monoalkylbenzene is ethylbenzene.

Further, in the process of the present invention, the gas stream comprising oxygen and monoalkylbenzene should be contacted with a liquid stream which comprises a naphthalene compound. Preferably, said naphthalene compound is naphthalene, alkylated naphthalene or a mixture thereof. Further, the alkylated naphthalene is preferably a naphthalene which is substituted with one or more $C_{1-4}$ alkyl groups, preferably a methyl group and/or ethyl group. Examples of suitable monoalkylated naphthalenes are 1-methylnaphthalene, 2-methylnaphthalene, 1-ethylnaphthalene and 2-ethylnaphthalene. An example of a suitable multialkylated naphthalene is 2,7-dimethylnaphthalene. Where a mixture of naphthalene compounds is used, the relative amounts of the naphthalene compounds may differ within wide ranges. The liquid stream comprising a naphthalene compound may comprise a mixture comprising naphthalene, 1-methylnaphthalene and 2-methylnaphthalene in amounts of from 1 to 20 wt. % (preferably 5 to 15 wt. %), 1 to 20 wt. % (preferably 5 to 15 wt. %) and 10 to 30 wt. % (preferably 15 to 25 wt. %), respectively, based on total weight of the naphthalene compounds, the remainder of the naphthalene compounds in said mixture being higher alkylated naphthalenes. An example of a suitable, commercially available liquid comprising a naphthalene compound is Solvesso® 200 from ExxonMobil Chemical, which comprises a mixture of naphthalene ($C_{10}$ compound), 1-methylnaphthalene and 2-methylnaphthalene ($C_{11}$ compounds) and higher alkylated naphthalenes ($C_{12}$, $C_{13}$ and $C_{14}$ compounds).

The amount of oxygen gas in the gas stream comprising oxygen and monoalkylbenzene to be contacted with the liquid stream in the present process may be in the range of from 1 to 10 wt. %, preferably 2 to 8 wt. %, more preferably 3 to 7 wt. % and most preferably 4 to 6 wt. %. Further, in said gas stream, the amount of monoalkylbenzene may be in the range of from 0.1 to 20 wt. %, preferably 0.2 to 15 wt. %, more preferably 0.5 to 10 wt. % and most preferably 1 to 6 wt. %. Nitrogen gas may be present in said gas stream in an amount of from 70 to 95 wt. %, preferably 80 to 90 wt. %. Water may be present in said gas stream in an amount of from 1 to 10 wt. %, preferably 1 to 5 wt. %. Other contaminants, such as methane, acetaldehyde, propionaldehyde, methanol, benzene and toluene may be present in said gas stream in amounts smaller than 0.5 wt. %, preferably smaller than 0.1 wt. %.

In order to effect an efficient transfer of monoalkylbenzene from the gas stream to the liquid stream comprising a naphthalene compound, it is preferred that the gas stream and liquid stream are contacted counter-currently. However, a co-current operation is also feasible. In a case where the contacting is effected counter-currently and in a vertical column, preferably the gas stream is fed to the bottom of the column and the liquid stream to the top of the column. However, a horizontal column may also be used, in which case it is preferred that the gas stream is fed to the column at various points at the bottom and the liquid stream is fed at one point, either on the lefthand side or on the righthand side in the longitudinal direction.

Where a vertical column is used as the absorber column in the present invention, the gas phase may be completely dispersed in a continuous liquid phase using a bubble column. In the latter case, there is question of a so-called "liquid-full" column, as may be the case in an absorber column wherein no sieve trays are positioned. However, in the present invention, such vertical absorber column does not have to be completely filled with liquid but a continuous gas phase and a continuous liquid phase may be present therein at the same time. In fact, operating the column such that it is not liquid-full, is preferred. Sieve trays may be positioned within the vertical absorber column. Examples of suitable absorber columns are disclosed in "Mass-Transfer Operations", Robert E. Treybal, McGraw-Hill Book Company, 1980, pages 139-142 and 158-171. A particular suitable absorber column containing sieve trays is disclosed in FIG. 6.8 at page 159 of said publication. Said publication is herein incorporated by reference.

In the present invention, the temperature in said absorber column may be of from 20 to 80° C., preferably of from 30 to 70° C., more preferably of from 40 to 60° C. Further, in the present invention, the pressure in said absorber column may be of from 0.1 to 10 bar gauge, preferably of from 0.5 to 5 bar gauge, more preferably of from 1.5 to 3.5 bar gauge.

The present process results in a liquid stream comprising monoalkylbenzene originating from the gas stream and the naphthalene compound and a gas stream comprising oxygen. It is possible that said liquid stream is separated into a fraction comprising monoalkylbenzene and a fraction comprising the naphthalene compound. The latter fraction may then be used again as a liquid absorbent stream in the present process. Such separation may for example be achieved in a distillation column under conditions known to anyone skilled in the art. As is demonstrated in the Example below, ethylbenzene can advantageously be separated at high yield from a liquid fraction comprising absorbed ethylbenzene and a mixture of naphthalene compounds.

As mentioned above, the gas stream comprising oxygen and monoalkylbenzene may have originated from a process wherein the monoalkylbenzene is oxidised with oxygen into an alkyl phenyl hydroperoxide. Therefore, the present invention also relates to a process for preparing alkyl phenyl hydroperoxide comprising:
(i) reacting monoalkylbenzene into alkyl phenyl hydroperoxide using an oxygen containing gas as the oxidant;
(ii) separating the reaction mixture into a liquid stream comprising alkyl phenyl hydroperoxide and monoalkylbenzene and a gas stream comprising oxygen and monoalkylbenzene;
(iii) contacting the gas stream comprising oxygen and monoalkylbenzene with a liquid stream comprising a naphthalene compound as described above, resulting in a liquid stream comprising monoalkylbenzene originating from the gas stream and the naphthalene compound and a gas stream comprising oxygen.

Preferably, between the above-mentioned steps (ii) and (iii), the majority of the monoalkylbenzene as contained in the gas stream comprising oxygen and monoalkylbenzene obtained in said step (ii) is condensed, for example by mixing with cold ethylbenzene or by cooling with cooling water in a heat exchanger. In this way, the load of ethylbenzene to be absorbed in the next step (iii) is reduced.

The liquid stream obtained in above-mentioned step (iii) is preferably separated into a first fraction comprising monoalkylbenzene and a second fraction comprising the naphthalene compound. Preferably, said first fraction is recycled to above-mentioned step (i), so that said monoalkylbenzene is advantageously not lost as valuable starting material for said step (i). Further, preferably, said second fraction is recycled to above-mentioned step (iii), so that this can advantageously be re-used as an absorbent.

As already mentioned above in connection with the process for recovering monoalkylbenzene from a gas stream comprising oxygen and monoalkylbenzene in general, in the above-mentioned process for preparing alkyl phenyl hydroperoxide, preferably, the monoalkylbenzene is ethylbenzene, the alkyl phenyl hydroperoxide is ethylbenzene hydroperoxide and the liquid absorbent stream comprises a mixture comprising naphthalene, 1-methylnaphthalene, 2-methylnaphthalene and higher alkylated naphthalenes ($C_{12}$, $C_{13}$ and $C_{14}$ compounds). Regarding above-mentioned step (iii), further reference is made to the above discussion of the process for recovering monoalkylbenzene from a gas stream comprising oxygen and monoalkylbenzene in general. The same preferences are applicable to said step (iii).

Regarding above-mentioned steps (i) and (ii) of the process for preparing alkyl phenyl hydroperoxide, reference is made to WO2006024655 and WO2008058925 which disclose suitable conditions for carrying out said steps (i) and (ii). WO2006024655 and WO2008058925 are herein incorporated by reference. Other suitable conditions known to anyone skilled in the art may also be applied.

The invention is further illustrated by the following Example.

EXAMPLE

In this Example, the set-up as shown in FIG. 1 is used to recover ethylbenzene (FE) from a gas stream comprising ethylbenzene, oxygen and nitrogen.

Referring to FIG. 1, a gas stream comprising nitrogen (84 wt. %), oxygen (5 wt. %), ethylbenzene (4 wt. %), water (4 wt. %) and methane, acetaldehyde, propionaldehyde, methanol, benzene and toluene in amounts smaller than 0.5 wt. %, is fed to the bottom of column 10 via line 1 at a flow rate of 106,000 g/h.

Via line 2, a liquid stream comprising 1-methylnaphthalene, 2-methylnaphthalene, 2,7-dimethylnaphthalene and 2-ethylnaphthalene, and a trace of EB (0.1 wt. %), is fed to the top of column 10. Said gas stream and liquid stream flow counter-currently through column 10. By this operation, EB is absorbed from the upwardly flowing gas stream into the downwardly flowing liquid stream. In column 10, the temperature is 50° C. and the pressure is 2.5 bar gauge. An EB-depleted gas stream leaves the top of column 10 and is removed as off-gas via line 3. Further, an EB-enriched liquid stream leaves the bottom of column 10 and is sent to column 11 via line 4.

In column 11, which is a distillation column, the EB-enriched liquid stream is heated at a bottom temperature of 250° C. and a top pressure of 0.5 bar gauge. An EB-depleted liquid stream leaves the bottom of column 11 and is sent to a reboiler (not shown in FIG. 1). The gas stream from said reboiler is recycled to the bottom of column 11. The liquid stream from said reboiler is cooled by passing through a heat-exchanger (not shown in FIG. 1), and is recycled to column 10 via line 2. A make-up stream comprising 1-methylnaphthalene (50 wt. %), 2-methylnaphthalene (30 wt. %), 2,7-dimethylnaphthalene (14 wt. %) and 2-ethylnaphthalene (6 wt. %) is fed to line 2 via line 5. Before entering the top of column 10, a portion of the liquid stream in line 2 is split off as a bleed-stream via line 6, in order to prevent build-up of high molecular weight contaminants in said liquid absorbent stream.

Further, a gas stream comprising EB leaves the top of column 11 and is sent to condenser 12 via line 7. The gas stream from condenser 12 is removed as off-gas via line 8. The liquid EB stream from condenser 12 is split into a first stream which is recycled to the top of column 11 and a second stream which is removed via line 9.

In the following table, the flow rate for EB and the flow rate for the absorbent (mixture of 1-methylnaphthalene, 2-methylnaphthalene, 2,7-dimethylnaphthalene and 2-ethylnaphthalene) in the streams of each of lines 1, 2, 3, 5, 6, 8 and 9 are mentioned.

|  | EB (g/h) | absorbent (g/h) |
| --- | --- | --- |
| stream in line 1 | 4,354 | 0 |
| stream in line 2 between exit of column 11 and connection with line 5 | 88.4 | 89,657 |
| stream in line 3 | 22.7 | 230 |
| stream in line 5 | 0 | 300 |
| stream in line 6 | 0 | 70 |
| stream in line 8 | 12.7 | <1 |
| stream in line 9 | 4,319 | <1 |

From the above table, it can be concluded that the liquid stream comprising a mixture of naphthalenes is an excellent absorbent for absorbing EB from a gas stream comprising ethylbenzene (EB), oxygen and nitrogen. Of the EB introduced into column 10 of FIG. 1 via line 1, 99.5 wt. % of EB is absorbed into the absorbent. Further, of said amount of EB introduced, 99.2 wt. % of EB is finally recovered via line 9 after separation of the absorbent from the EB in column 11.

What is claimed is:

1. A process for recovering monoalkylbenzene from a gas stream comprising oxygen and monoalkylbenzene, wherein the gas stream comprising oxygen and monoalkylbenzene is contacted with a liquid stream comprising a naphthalene compound.

2. The process according to claim 1, wherein the monoalkylbenzene is a benzene which is substituted with an alkyl substituent which is a linear or branched $C_1$-$C_4$ alkyl group, including ethyl, iso-propyl and sec-butyl.

3. The process according to claim 2, wherein the monoalkylbenzene is ethylbenzene.

4. The process of claim 1, wherein the naphthalene compound is naphthalene, alkylated naphthalene or a mixture thereof.

5. The process according to claim 4, wherein the alkylated naphthalene is a naphthalene which is substituted with one or more $C_{1-4}$ alkyl groups, preferably a methyl group and/or ethyl group.

6. The process of claim 1, wherein the gas stream and the liquid stream are contacted counter-currently.

7. The process according to claim 6, wherein the gas stream is fed to the bottom of a vertical column and the liquid stream is fed to the top of said column 8. The process of claim 1, resulting in a liquid stream comprising monoalkylbenzene originating from the gas stream and the naphthalene compound and a gas stream comprising oxygen, wherein said liquid stream is separated into a fraction comprising monoalkylbenzene and a fraction comprising the naphthalene compound.

9. A process for preparing alkyl phenyl hydroperoxide comprising:
   (i) reacting monoalkylbenzene into alkyl phenyl hydroperoxide using an oxygen containing gas as the oxidant;
   (ii) separating the reaction mixture into a liquid stream comprising alkyl phenyl hydroperoxide and monoalkylbenzene and a gas stream comprising oxygen and monoalkylbenzene;

(iii) contacting the gas stream comprising oxygen and monoalkylbenzene with a liquid stream comprising a naphthalene compound in accordance with claim 1, resulting in a liquid stream comprising monoalkylbenzene originating from the gas stream and the naphthalene compound and a gas stream comprising oxygen.

10. The process according to claim 9, wherein the liquid stream obtained in step (iii) is separated into a fraction comprising monoalkylbenzene and a fraction comprising the naphthalene compound.

11. The process according to claim 10, wherein the fraction comprising monoalkylbenzene is recycled to step (i).

12. The process according to claim 10, wherein the fraction comprising the naphthalene compound is recycled to step (iii).

\* \* \* \* \*